United States Patent [19]

Patel et al.

[11] 3,999,946

[45] Dec. 28, 1976

[54] TIME-TEMPERATURE HISTORY INDICATORS

[75] Inventors: Gordhanbhai N. Patel, Morris Plains; Anthony F. Preziosi, Ledgewood; Ray H. Baughman, Morris Plains, all of N.J.

[73] Assignee: Allied Chemical Corporation, Morris Township, N.J.

[22] Filed: Feb. 23, 1976

[21] Appl. No.: 660,562

[52] U.S. Cl. .............................. 23/253 TP; 426/88
[51] Int. Cl.$^2$ ........................................ G01N 31/22
[58] Field of Search ........... 23/253 TP; 426/87, 88; 73/356; 116/114 AM

[56] References Cited

UNITED STATES PATENTS

| | | | |
|---|---|---|---|
| 3,344,670 | 10/1967 | Olsen et al. | 23/253 TP |
| 3,615,719 | 10/1971 | Michel et al. | 426/88 |
| 3,768,976 | 10/1973 | Hu et al. | 23/253 TP X |
| 3,822,134 | 7/1974 | Rasch et al. | 427/248 A X |
| 3,942,467 | 3/1976 | Witonsky | 426/88 X |

Primary Examiner—Robert M. Reese
Attorney, Agent, or Firm—David W. Collins; Ernest A. Polin

[57] ABSTRACT

Compositions containing at least two conjugated acetylene groups (-C ≡ C-C ≡ C-) are suitable as integral time-temperature history indicators. These compositions exhibit sequences of irreversible color changes at combinations of times and temperatures specific to each composition. Thus, when supported on the surface of a product or on a substrate affixed to a product, they are useful for indicating whether a perishable (e.g., foodstuff, pharmaceutical, chemical, etc.) has been exposed to an undesirable time-temperature history that results in substantial degradation of the perishable or whether a product has been exposed to a desirable time-temperature history during processing (e.g., the sterilization of a foodstuff or biomedical material).

19 Claims, 2 Drawing Figures

TIME-TEMPERATURE HISTORY INDICATORS

BACKGROUND OF THE INVENTION

1. Field of the Invention

This invention relates to visual, irreversible time-temperature history indicators useful for indicating whether perishables, such as foodstuffs, pharmaceuticals, chemicals, photographic films and the like, have experienced undesirable time-temperature histories which result in substantial degradation or whether products have been exposed to desirable time-temperature histories during processing.

2. Description of the Prior Art

The need to know whether a product has been exposed either to an undesirable time-temperature history which results in substantial degradation or to a correct time-temperature history required during processing is self-evident. This applies, for example, to frozen foods, pharmaceuticals or photographic films which may be exposed to undesirable high temperatures for significant time periods during storage and distribution. This also applies to canned goods and biomedical materials, which must be held at high temperatures for a specific time period in an autoclave to guarantee sterilization.

A number of patents have issued disclosing indicators useful, for example, in detecting whether frozen foods have been exposed either to time-temperature combinations or to a particular temperature which results in substantial degradation. U.S. Pat. No. 2,553,369, issued May 15, 1951 to S. Hoffman, discloses a time-temperature indicator comprising a combination of hydrated potassium triiodide, a soluble starch and a diastase. At temperatures above freezing, the diastase (which is a starch-digesting enzyme) hydrolyzes the starch, thereby altering the blue color initially rendered to the starch by the potassium triiodide.

U.S. Pat. No. 2,892,798, issued June 30, 1959 to D. L. Dobbs et al., discloses an irreversible temperature indicator for frozen foods comprising an aqueous solution of mercuric and cuprous iodide colloidally dispersed in a liquid phase comprising an alkali metal iodide. Upon exposure to thawing temperatures, a color change occurs.

U.S. Pat. No. 3,545,400, issued Dec. 8, 1970 to V. L. Smith, discloses a freeze and thaw indicator which is activated by rupture of a dye-filled container upon freezing. Upon thawing, the released dye flows onto an absorbent pad, thereby providing the positive indicator response.

U.S. Pat. No. 3,768,976, issued Oct. 30, 1973 to K. H. Hu et al., discloses a process for constructing a time-temperature history indicator. The operation of this indicator depends upon the rate of permeation of oxygen through a polymer envelope containing an aqueous solution of a redox red dye. Upon oxidation, the red dye turns colorless, providing the warning signal that the perishable has been exposed to too high a temperature for too long a time period.

U.S. Pat. No. 3,844,718, issued Oct. 29, 1974 to H. Cohen, discloses a defrost indicator which is activated by the contact of water or water vapor with a water-soluble ink supported on a hygroscopic substrate.

Indicators have also been disclosed for high temperature applications; see, for example, U.S. Pat. No. 1,668,767, issued May 8, 1928 to J. Hansen et al., which discloses a process for indicating whether cans filled with food have been exposed to sufficiently high cooking temperatures. The process comprises marking the cans with a colored substance which changes color at 212° F. The coloring substance is an organic color such as erythrocine in a binder, such as shellac, and a solvent, such as grain alcohol.

U.S. Pat. No. 3,078,182, issued Feb. 19, 1963 to J. W. Crone, Jr., et al., discloses a color-changing pressuresensitive adhesive indicator tape for indicating whether sterilization of packages has occurred. The indicator comprises a mixture of a halogen-containing binder resin and a heat sensitive heteropolymolybdate pigment.

The foregoing references are representative of many patents in this area. A drawback of many of the indicators in the prior art is, however, that they are useful only over very limited temperature ranges, such as within a few degrees of the freezing point of water, or that they are bulky or expensive, or that they depend on diffusion or on complex reaction mechanisms for their operation. Furthermore, most of these indicators do not provide a direct measure of time-temperature history. This is most important, since both proper product processing and degradation of perishables often depend on the time exposure to particular temperatures. For example, food exposed for a period of time at one temperature may degrade to the same extent as if exposed for a shorter period processing time at a higher temperature. Similarly, high temperature according for a short period of time may achieve the same effect as lower temperature processing for a longer period of time. Thus, the time-temperature history to which an article has been exposed is often more critical than whether it has been exposed to a particular undesirable degradation temperature or to a desirable processing temperature. Indicator materials are consequently required which match the time-temperature degradation characteristics of a wide range of perishables and the time-temperature characteristics of a wide range of production processes.

Accordingly, it is often desirable that a time-temperature indicator should undergo a series of readily detectable changes corresponding to the progressive development of time-temperature history. Thus, the indicator should preferably be used to denote the integral, or sum total, of thermal exposure (time and temperature), rather than merely that a particular temperature has been exceeded. Many of the indicators disclosed in the prior art are not capable of denoting integral time-temperature behavior.

Finally, many of the indicators disclosed in the prior art are not conveniently activated or deactivated. If the indicator cannot be conveniently activated, preusage storage of the active indicator can become a problem. Only if time-temperature history development can be conveniently halted, is it possible to obtain permanent indicator responses at various points in the storage and distribution of a perishable or the processing of a product.

There are many materials that evidence an irreversible color change upon exposure to temperature. For example, polyacetylenes having at least two conjugated acetylene groups have been disclosed in U.S. Pat. No. 3,822,134, issued July 2, 1974 to A. A. Rasch et al., for use as vacuum-deposited radiation-sensitive elements. Some of these radiation sensitive elements evidence an irreversible color change upon exposure to temperature. However, such a color change, by itself, is insufficient to suggest its use as a practical time-temperature history indicator, since the color change may simply indicate that a particular temperature has been exceeded, without an indication either of the length of time that temperature has been exceeded or of the time averaged exposure at higher temperatures. Further, in order to construct a readily readable indicator, a sharp color change which occurs in a narrow time interval for each of a range of exposure temperatures is required.

Practical indicators accumulate a time-temperature history in integrated form as a single reading. Desirably, such indicators should parallel the reaction of the particular perishable product to which they are attached to changes in temperatures over periods of time.

SUMMARY OF THE INVENTION

In accordance with the invention, there is provided a process of applying to a perishable product an integral time-temperature history indicator comprising at least one acetylenic compound having at least two conjugated acetylene groups ($-C \equiv C-C \equiv C-$) per molecule. Further, there is provided a perishable product having attached thereto an integral time-temperature history indicator comprising at least one acetylenic compound having at least two conjugated acetylene groups per molecule.

Such acetylenic compounds accumulate a time-temperature history in integrated form as a single reading. Depending upon the particular application, acetylenic compounds can be selected that parallel the response of the perishable product to which they are attached to changes in temperatures over periods of time. The time-temperature history indicator composition is either deposited on the surface of the perishable product (self-supported) or deposited on a substrate affixed to the perishable product and is conveniently applied by melt, vapor, or solution crystallization. The term "applied to" employed in the appended claims is intended to include both of the aforesaid deposition procedures. The indicator response results from a series of relatively abrupt color changes which occur upon the progressive development of time-temperature history.

DETAILED DESCRIPTION OF THE INVENTION

Figure 1:
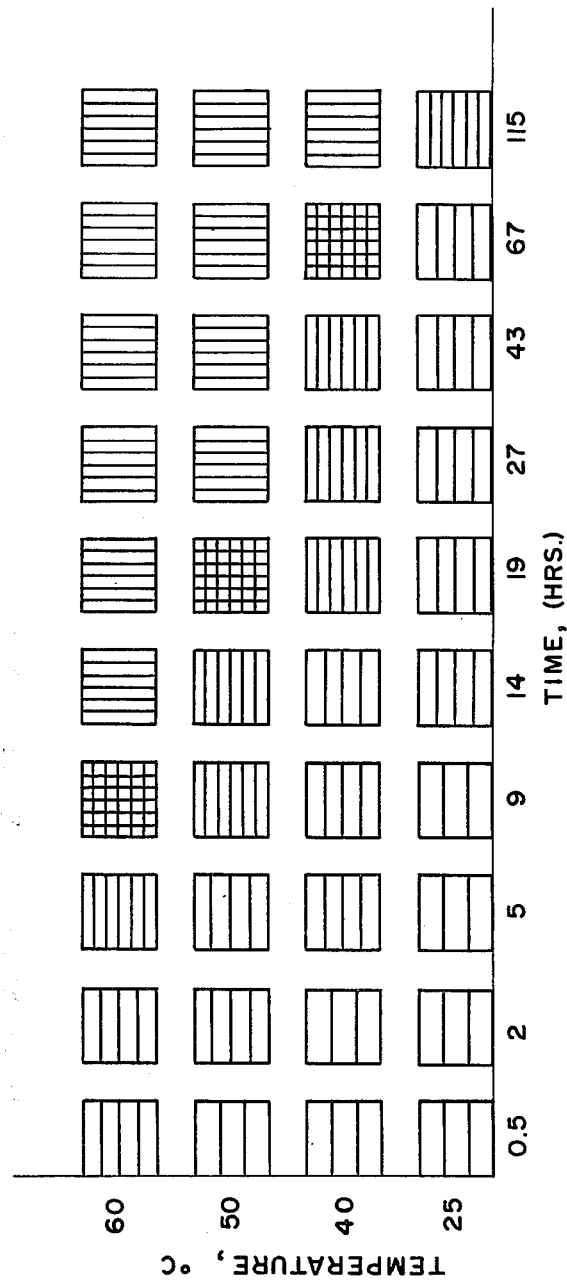
FIG. 1 is a representation of color changes obtained for a time-temperature history indicator (comprising 2,4-hexadiyne-1,6-diol-bisphenylurethane deposited on filter paper by the evaporation of the solvent, p-dioxane, from an absorbed solution) after exposure at the times and temperatures denoted.

In accordance with the invention, there is provided a process of applying to a perishable product an integral time-temperature history indicator comprising at least one acetyenic cómpound having at least two conjugated acetylene groups ($-C \equiv C-C \equiv C-$) per molecule. Further, there is provided a perishable product having attached thereto an integral time-temperature history indicator comprising at least one acetylenic compound having at least two conjugated acetylene groups per molecule. Such acetylenic compounds accumulate a visual and irreversible time-temperature history in integrated form as a single reading. Particular acetylenic compounds can be matched to particular perishable products to parallel the response of the product to changes in temperatures over periods of time. As used herein, the term "perishable product" refers to package frozen foods, dairy products, meat, pharmaceuticals, photographic film, canned goods and the like. The processes monitored by the acetylenic compositions include undesirable degradation and desirable processing of these products.

The acetylenic compound may be monomeric or polymeric, cyclic or acyclic, so long as it contains at least two conjugated acetylene groups. Examples of suitable acetylenic compounds include diynes, triynes, tetraynes and hexaynes. In the simplest case monomers are of the form $R-C \equiv C-C \equiv C-R$, where R is a substituent group, while polymers are of the form $(-C \equiv C-C \equiv C-R-)_n$, where n has a high value. Examples of R groups include alkyl, aryl, benzoates, sulfonates, urethanes, acids, alcohols and the like. These indicator materials include homopolymers and copolymers containing $(-C \equiv C-)_m$ functionalities (where m is equal to or greater than 2) either in the backbone, or side groups or both. Preferred acetylenic compounds include diynes, triynes, tetraynes and hexaynes. Preferred derivatives include mono and bis sulfonates, mono and bis urethanes, mono and bis acids and mono and bis alcohols of acetylenic compounds. Such preferred compounds and derivatives are most useful as time-temperature history indicators over the times and temperatures likely to be experienced by commercial perishable products. Examples of acetylenic compounds useful as indicator compositions in the practice of the invention include:

A. SULFONATES 1. p-$CH_3$-$CH_6H_4SO_3CH_2$-C $\equiv$ C-C $\equiv$ C-$CH_2SO_3C_6H_4$-p-$CH_3$  2,4-hexadiyne-1,6-diol-bis-p-toluene sulfonate
2. p-$CH_3$-$C_6H_4SO_3CH_2$-C $\equiv$ C-C $\equiv$ C-$(CH_2)_2$-C $\equiv$ CH 2,4,8-nonatriyne-1-ol-p-toluene sulfonate
3. [p-$CH_3$-$C_6H_4SO_3CH_2$C $\equiv$ C-C $\equiv$ C-$(CH_2)_2$-C $\equiv$ C-$]_2$  2,4,8,10,14,16-octadecahexayne-1,18-diol-bis-p-toluene sulfonate

B. URETHANES

1. $C_6H_5NHOCOCH_2$-C $\equiv$ C-C $\equiv$ C-$CH_2OCONHC_6H_5$ 2,4-hexadiyne-1,6-diol-bisphenylurethane
2. $C_2H_5NHOCOCH_2$-C $\equiv$ C-C $\equiv$ C-$CH_2OCONHC_2H_5$ 2,4-hexadiyne-1,6-diol-bisethylurethane
3. $C_4H_9NHOCOCH_2$-C $\equiv$ C-C $\equiv$ C-$CH_2OCONHC_4H_9$ 2,4-hexadiyne-1,6-diol-bis-n-butylurethane
4. $C_6H_5(CH_2)_2C \equiv$ C-C $\equiv$ C-$CH_2OCONHC_2H_5$ 7-phenyl-2,4-heptadiyne-1-ol-ethylurethane
5. $C_2H_5NHOCO(CH_2)_2$-C $\equiv$ C-C $\equiv$ C-$(CH_2)_2OCONHC_2H_5$  3,5-octadiyne-1,8-diol-bisethylurethane
6. $CH_3NHOCO(CH_2)_4$-C $\equiv$ C-C $\equiv$ C-$(CH_2)_4OCONHCH_3$  5,7-dodecadiyne-1,12-diol-bismethylurethane
7. $C_6H_5NHOCO(CH_2)_4$-C $\equiv$ C-C $\equiv$ C-$(CH_2)_4OCONHC_6H_5$  5,7-dodecadiyne-1,12-diol-bisphenylurethane 8. $CH_3NHOCOCH_2\text{-}C \equiv C\text{-}C \equiv C\text{-}(CH_2)_2\text{-}C \equiv CH$ 2,4,8-nonatriyne-1-ol-methylurethane
9. $C_2H_5NHOCOCH_2\text{-}C \equiv C\text{-}C \equiv C\text{-}(CH_2)_2\text{-}C \equiv CH$ 2,4,8-nonatriyne-1-ol-ethylurethane
10. $C_2H_5NHOCOCH_2\text{-}C \equiv C\text{-}C \equiv C\text{-}C \equiv C\text{-}CH_2OCONHC_2H_5$ 2,4,6,8-decatetrayne-1,10-diol-bisethylurethane
11. $CH_3NHOCO\text{-}C \equiv C\text{-}C \equiv C\text{-}(CH_2)_2\text{-}C \equiv C\text{-}C \equiv C\text{-}OCONHCH_3$ 2,4,8,10-dodecatetrayne-1,12-diol-bismethylurethane
12. $C_2H_5NHOCOCH_2\text{-}C \equiv C\text{-}C \equiv C\text{-}(CH_2)_2\text{-}C \equiv C\text{-}C \equiv C\text{-}CH_2OCONHC_2H_5$ 2,4,8,10-dodecatetrayne-1,12-diol-bisethylurethane
13. $C_6H_5NHOCOCH_2\text{-}C \equiv C\text{-}C \equiv C\text{-}(CH_2)_2\text{-}C \equiv C\text{-}C \equiv C\text{-}CH_2OCONHC_6H_5$ 2,4,8,10-dodecatetrayne-1,12-diol-bisphenylurethane
14. $[CH_3NHOCOCH_2\text{-}C \equiv C\text{-}C \equiv C\text{-}(CH_2)_2\text{-}C \equiv C\text{-}]_2$ 2,4,8,10,14,16-octadecahexayne-1,18-diol-bismethylurethane
15. $[C_2H_5NHOCOCH_2\text{-}C \equiv C\text{-}C \equiv C\text{-}(CH_2)_2\text{-}C \equiv C\text{-}]_2$ 2,4,8,10,14,16-octadecahexayne-1,18-diol-bisethylurethane
16. $[C_6H_5NHOCOCH_2\text{-}C \equiv C\text{-}C \equiv C\text{-}(CH_2)_2\text{-}C \equiv C\text{-}]_2$ 2,4,8,10,14,16-octadecahexayne-1,18-diol-bisphenylurethane

C. OTHER

1. $HOOC(CH_2)_8C \equiv C\text{-}C \equiv C\text{-}CH_2OH$ 10,12-tetradecadiynoic acid-14-ol Similarly suitable for the practice of the invention are cyclic compositions such as

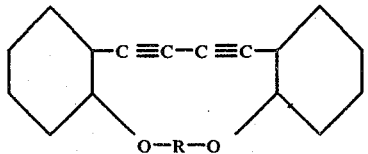

where R is $-CO(CH_2)_3CO-$, $-CO(CH_2)_4CO-$, $-(CH_2)_3-$, $-CH_2CH=CHCH_2-$ (cis or trans), $-CH_2C\equiv CCH_2-$ or $-CH_2(m\text{-}C_6H_4)CH_2-$.

All acetylenic compounds (monomeric or polymeric) containing at least two conjugated acetylene groups which polymerize in the solid state when thermally annealed are useful in the practice of the invention. The color changes which give rise to the thermal response of the indicator usually correspond to addition reactions which transform one or more of the conjugated acetylenic functionalities in an acetylenic compound or in a mixture thereof to fully conjugated chains of the type $(=C\text{-}(C \equiv C)_r\text{-}C=)_q$, where $q$ corresponds to the number of mutually reacting acetylenic functionalities, which is dependent upon reaction conditions, and where $r$ is 1 or larger. The intense coloration of the polymerized materials results from the fully conjugated chains.

The acetylenic compounds may be prepared by known methods. For example, the mono- and bis-urethane derivatives may be prepared by reacting the corresponding diyne-ol or diyne-diol with an isocyanate having the formula RNCO. Examples of R include $C_6H_5(CH_2)_r-$, $CH_3(CH_2)_r-$, and $C_{10}H_7(CH_2)_r-$, where $r$ is an integer, typically from 0 to 11. Thus, for example, 2,4-hexadiyne-1-ol-methylurethane may be prepared by reacting 1-hydroxy-2,4-hexadiyne with methylisocyanate, and 3,5-octadiyne-1,8-diol-bis-α-naphthylurethane may be prepared by reacting 3,5-octadiyne-1,8-diol with α-naphthyl isocyanate. A catalyst may be added to the reaction mixture to increase the reaction rate to produce the desired acetylenic compound. Conventional tin catalysts (e.g., dibutyl-tin-di-2-ethylhexoate) and tertiary amines (e.g., triethyl amine) may be used as catalysts. The reaction mixture may also be warmed, as for example, to about 45° to 55° C to speed up the reaction, which is usually moderately exothermic. Such heating, however, is not required. The desired diyne-ol or diyne-diol may also be prepared by conventional methods. Thus, for example, 4,6-decadiyne-1,10-diol may be prepared by the oxidative coupling of the corresponding alkyne, i.e. 4-pentyne-1-ol.

Following preparation of the desired acetylenic compound, it must be crystallized from an appropriate solvent, from the melt, or from the vapor, so as to provide an active phase. Suitable solvents include, for example, alkyl esters of monocarboxyl acids, alkyl alcohols, paraffins, olefins, benzene, alkylated benzenes, ethers, ketones, petroleum ether, halogenated hydrocarbons and water. Particularly useful crystallizing solvents are 1,2-dimethoxyethane, petroleum ether, acetone, chloroform, benzene, methanol, ethanol, xylene, ethylacetate and water. Crystallization may, for example, be effected by room temperature evaporation of solutions containing from 0.0001 to 0.5 parts by weight of monomer per part by weight of solvent or solvent blend. Alternatively, other conventional crystallization procedures may be used, such as sublimation, mixing of solvent and non-solvent, or cooling a saturated solution to a sufficiently low temperature (usually above about −30° F) such that the required crystallization occurs.

It is important to select the proper solvent for crystallization, since some solvents result in a more active indicator material and other solvents result in a less active indicator material. A more active indicator material changes color at a lower temperature in a shorter period of time than a less active indicator material. For example, the compound $[C_6H_5NHOCOCH_2\text{-}C \equiv C\text{-}]_2$, when crystallized from a 20% solution in p-dioxane, becomes deep blue after 3 hr at 60° C and transforms from deep blue to dark red after 9 hr at this temperature. By comparison, the same compound, when crystallized from a 20% solution in bromoform, turns a light pink after 16 hr at 70° C. Similarly, different phases with various reactivities may be obtained by variations in melt crystallization or vapor deposition conditions.

For obtaining acetylenic compounds of the invention with highest thermal reactivities, several approaches may be followed. Composition reactivities tend to increase substantially with increasing values of $n$ in the functionality $(-C \equiv C\text{-})_n$. Similarly, decreasing the size and number of unreactive functionalities in the composition tends to increase reactivity, as does increasing ring strain in compositions having cyclic structures. Alternatively, extremely high reactivity indicator compositions can be obtained by low temperature exposure of acetylenic compounds to actinic radiation (such as γ-rays, electron beams, ultraviolet radiation and X-rays). This processing introduces reactive centers which propagate as a function of time-temperature history, thereby producing color changes.

The thermal reactivity of certain acetylenic compounds can be dramatically increased by low temperature exposure to actinic radiation, such as $Co^{60}$ γ-ray radiation. For example, the initially colorless compound $[C_6H_5NHOCO(CH_2)_4-C \equiv C-]_2$, when crystallized from a cooled, saturated ethyl acetate solution and exposed at $-196°$ C to 50 Mrad of $Co^{60}$ γ-rays at a dosage of 1 Mrad/hr, is tan colored immediately after irradiation and irreversibly turns reddish bronze within 5 to 10 min after removal from that temperature to ambient temperature.

For certain compounds, the reactivity of similarly irradiation-activated material is so high that substantial reaction, along with the associated color changes, occurs in less than 2 days at liquid nitrogen temperature ($-196°$ C). This behavior has been observed for the initially colorless phase of $[C_2H_5NHOCO(CH_2)_3-C \equiv C-]_2$ obtained by crystallization from ethyl acetate. This composition, when activated with 50 Mrad of γ-rays, turns deep blue within 50 hr at $-196°$ C.

The thermal reactivity of acetylenic compounds of the invention can also be increased by adding a suitable conventional initiator. Examples of conventional initiators include alkyl peroxides such as dicumyl peroxide, azo compounds such 2-t-butylazo-2-cyano propane, diacyl peroxides such as benzoyl peroxide, hydroperoxides such as cumene hydro peroxide, ketone peroxides such as cyclohexanone peroxide and peroxyesters such as t-butyl peroxyacetate. The thermal reactivity can be decreased by adding a suitable conventional inhibitor. Examples include quinones such as benzoquinone, and aromatic nitro-compounds such as m-nitrobenzene and 2,4-dinitrochlorobenzene.

The time-temperature history indicator is prepared by depositing an acetylenic compound or a mixture of acetylenic compounds on a substrate which is affixed to the perishable product. Alternatively, the perishable product itself may serve as the substrate. The substrate may be porous or nonporous. Typical examples include paper, cardboard, wood, glass, ceramics, plastics and metals.

Both the range of color change and the composition reactivity can be varied by codeposition of different acetylenic compounds (at least one of which contains at least two conjugated acetylene groups) or by the codeposition of one or more acetylenic compounds which contain at least two conjugated acetylene groups with one or more compounds which have similar molecular shape and polarity as the acetylenic compound, but which do not contain reactive acetylenic functionalities. Such codepositions can be from the vapor, melt or solution phases.

The acetylenic compounds are conveniently deposited from a solution, allowing the solvent to evaporate. While in solution, they are usually relatively inactive and will not change color, regardless of time or temperature. Once deposited as a solid on the substrate, however, they are then responsive to time-temperature exposures. Some compounds evidence color changes in a specified time period at comparatively low temperatures while others evidence comparable color changes in a similar time period only at comparatively high temperatures. In general, the acetylenic compounds within the scope of the invention evidence color changes within the range of $-180°$ to $+250°$ C for time periods of practical interest. Selection of both compound and solvent govern the actual time-temperature history indicating behavior.

The acetylenic compounds of the invention are also generally substantially inactive in the molten state and in the vapor state. Deposition on a substrate by melt solidification or vapor deposition results in an active phase that is responsive to time-temperature exposures.

In some cases, the acetylenic compounds are sensitive to exposure to short wavelength UV or UV-visible radiation. To construct an indicator material from such compounds, it may be desirable to incorporate a filter material with the indicator to eliminate undesirable photo-induced reactions. The UV reactivity evident for certain acetylenic compounds is substantially eliminated by protecting such compounds from exposure with a UV-absorbing film over the acetylenic compound. Conventional UV stabilizers are also useful for this purpose. Examples of UV stabilizers include benzophenones such as 2-hydroxy-4-methoxy benzophenone, benzotrazoles such as 2-(2'-hydroxy-5'-methylphenyl) benzotriazole, substituted acrylates such as ethyl-2-cyano-3,3-diphenyl acrylate and aryl esters such as phenyl salicylate.

The integral time-temperature history indicators in accordance with the invention are useful in a number of applications. For example, when affixed to containers of perishables, the indicators can be used to indicate whether the perishables have been exposed to thermal conditions which result in appreciable degradation. Likewise, indicators can be attached to individual cans to indicate whether canned goods have experienced desirable sterilization conditions. As another example, the indicator compositions can be dispersed in the polymeric insulation used for electrical wiring. Color changes of the composite insulator composition would then indicate that long term overheating is occurring which could lead to insulation breakdown or to combustion of surrounding materials.

To deactivate an indicator composition, a phase change from a highly active phase to a substantially inactive phase may be induced either by changing temperature above a critical limit, which is dependent upon composition, or by applying a mechanical stress.

Since the acetylenic compounds are usually inactive when molten, the indicator can be deactivated by heating to some temperature above the melting point of the unpolymerized material. In such a case, the heating step should be done rapidly, at a rate dependent upon the reactivity of the indicator composition, so that significant thermal reaction does not occur during the deactivation step.

Similarly, certain symmetrical acetylenic compounds with paraffinic sidegroups crystallize from the melt as thermally inactive phases. Upon cooling such a phase to a temperature $T_c$ which is between $-50°$ and $25°$ C, depending upon composition, a reversible phase transformation occurs to a thermally active phase. Consequently, the existence of this reversible phase transformation can be utilized to either activate or deactivate the indicator response.

The fact that many acetylenic compounds form phases in which non-acetylenic molecules enter interstitially or substitationally is useful in either activating or deactivating indicator response. For example, formation of donor-acceptor complexes between acetylenic compounds with donor sidegroups, such as aromatic groups, and acceptors, such as tetracyanoethylene or tetracyanoquinodimethane, is usually observed to transform a highly active to an inactive phase, although the addition of such materials in amounts substantially less than equimolar can increase phase reactivity. The decrease in reactivity results from the formation of the donor-acceptor complex, which forces the conjugated acetylene functionalities so far apart that neighboring acetylenic groups cannot thermally react. Consequently, indicator response can be either activated by disrupting donor-acceptor interactions, e.g., via heat or mechanical stress, or deactivated by forming such a complex, e.g., by exposure of the acetylenic compound to vapors or to a solution containing a complexing agent.

The stress-induced phase transformation of certain of these indicators may be utilized to "freeze" information so that further exposure to temperature no longer produces a color change. For example, the symmetrical benzoate of 2,4-hexadiyne-1,6-diol (R-C $\equiv$ C-C $\equiv$ C-R, where R is $-CH_2OCOC_6H_5$) is obtained as Phase I crystals by crystallizing a 1.3 to 23.8 wt% solution at 5° C in methanol. On the other hand, crystallization at the same temperature from diethyl ether solution results in either phase I or phase II crystals, depending upon concentration (about 12.3 wt% solution for the former and 17.4 to 29.6 wt% solution for the latter). Phase II crystals are thermally inactive, while phase I crystals have a low thermal reactivity usable for high temperature, long time period indicator applications (e.g., several years at temperatures above room temperature and below the melting temperature of 74.8° to 75.8° C.). Application of mechanical stress, as by striking, causes a phase transformation from the active phase I to the inactive phase II.

Further, the composition 2,4-hexadiyne-1,6-diol-bisphenyl urethane, represented by the formula $C_6H_5NHOCOCH_2-C \equiv C-C \equiv C-CH_2OCONHC_6H_5$, when crystallized from p-dioxane undergoes a stress-induced phase transformation to an inactive phase. Thus, a convenient tear-off indicator can be fabricated, which is stamped with code numbers at various points in the storage and distribution of perishables, for eventual evaluation of product handling procedures. The indicator regions under each stamp will be deactivated at the time of stamping, thereby providing permanent records on one indicator of the state of the perishable at various points from manufacture to eventual consumer purchase.

The indicator also can be deactivated by any process which removes the unreacted indicator composition, such as by sublimation or by solvent extraction. Further, a composition, such as bromine solution or vapor, which preferentially reacts with the unreacted acetylenic compounds, thereby eliminating the reactive conjugated acetylene groups employed in the indicator, is also used to deactivate the indicator.

For example, indicator tabs are deactivated by solvent extraction of unreacted indicator material, since the reaction product is typically insoluble in most conventional solvents. This is conveniently done using an indicator construction analogous to that used for instant photographic film development, whereby pulling a tab exposes the indicator composition to a solvent, which immobilizes the indicator response. A similar tab-like construction is also used to initiate indicator activity. In this case, pulling a tab exposes an inactive solution of an indicator composition to the atmosphere, permitting solvent evaporation and thereby forming the active indicator phase. In order to obtain the widest possible range of indicator response in one device, the indicator can consist of a mixture of different indicator compositions, each of which undergoes a series of color changes during thermal history development. Alternatively, the indicator can consist of adjacent strips containing different acetylenic compositions with different activities. A device which directly reads in terms of the equivalent storage time at a reference temperature can be constructed from such an array, via the propagation of a particular color change across members in the array.

In particular instances, it may be convenient to apply the indicator composition in the form of a printed message, which will not be readable on the chosen background until the color development corresponding to a specified thermal treatment is obtained.

EXAMPLES

In the examples below, the time-temperature histories of particular acetylenic compounds of the invention were observed by the following procedure. Squares of No. 42 Whitman filter paper were saturated with a solution of the respective compositions in an appropriate solvent (usually a B 20% by weight solution). Following solvent evaporation, each square was exposed to a particular temperature for a particular period of time.

EXAMPLE 1

A 20% solution of 2,4-hexadiyne-1,6-diol-bisphenylurethane, as represented by the formula $C_6H_5NHOCOCH_2-C \equiv C-C \equiv C-CH_2OCONHC_6H_5$, in p-dioxane was sprayed onto 1.5 × 1.5 inch squares of filter paper and the solvent was evaporated. The indicators thus obtained were annealed at −20°, 0°, 23°, 40°, 50°, and 60° C in the dark for various time periods. With the exception of those filter papers stored at −20° and 0° C, the filter papers were removed from their respective temperature environment at different times and stored at −20° C. At the completion of the experiment, the papers were mounted on a white paper background and photographed at 0° C. The following results were observed:

At −20° C, there was little development of color.

At 0° C, a light pale blue color developed very slowly.

At 23° C, a blue color developed and intensified, but did not change to a red color even after 40 days.

At 40° C, a blue color developed, intensified and changed to red after about 67 hr. The red color then intensified slightly with time.

At 50° C, a blue color developed rapidly and then changed to red after about 22 hr. The red color then intensified slightly with time.

At 60° C, a blue color developed very rapidly and then changed to red after about 8 hr. The red color then intensified slightly with time.

These color changes are schematically depicted in FIG. 1, which shows the colors developed by the squares of filter paper at the time and temperatures indicated. The relative spacing of lines is used to indicate intensity.

EXAMPLE 2

A 20% solution of 2,4-hexadiyne-1,6-diol-bis-p-toluene sulfonate, as represented by the formula p-$CH_3$-$C_6H_4SO_3CH_2-C \equiv C-C \equiv C-CH_2SO_3C_6H_4$-p-$CH_3$, in ethyl acetate was sprayed onto filter paper and the solvent was evaporated as in Example 1. The following results were observed:

At −20° C, no development of color occurred, even after 5 months.

At 23° C, a red color developed slowly, but did not change to a green-gold color even after 40 days.

At 40° C, a red color developed, intensified and changed to green-gold after about 250 hr.

At 50° C, a red color developed rapidly and intensified with time and changed to green-gold after about 85 hr.

At 60° C, a red color developed and intensified rapidly and changed to green-gold after about 32 hr.

At 70° C, a red color developed and intensified very rapidly and changed to green-gold after about 11 hr.

EXAMPLE 4

The following materials, deposited onto white filter paper as in Example 1 from solution in the solvents tabulated below, were tested at temperatures of −26°, 8°, 24° and 50° C. Color development was determined periodically by matching the indicator color to a Munsell Photometer chart (available from Munsell Color Co., Inc.) with the results listed in Table I below:

TABLE I

| Munsell Color Code | Temperature, ° C | | | |
|---|---|---|---|---|
| | −26° | −8° | 24° | 50° |
| 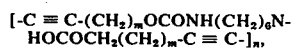[$CH_3NHOCOCH_2-C{\equiv}C-C{\equiv}C-CH_2-$]$_2$ (in methanol) | | | | |
| 5RP3/6 | | | | 25 d |
| 5RP4/12 | | | | 336 hr |
| 5RP5/10 | | | 25 d | 168 hr |
| 5RP6/10 | | | 72 hr | 6 hr |
| 5RP7/8 | | 79 d | 48 hr | 3 hr |
| 5RP8/6 | | 336 hr | 22 hr | 1 hr |
| 5RP9/2 | | 72 hr | 3 hr | 30 min |
| [$CH_3NHOCOCH_2-C{\equiv}C-C{\equiv}C-(CH_2)_2-C{\equiv}C-$]$_2$ (in acetone) | | | | |
| 5RP3/6 | | | | 336 hr |
| 5RP4/12 | | | 25 d | 72 hr |
| 5RP5/10 | | | 168 hr | 22 hr |
| 5RP6/10 | | 79 d | 30 hr | 6 hr |
| 5RP7/8 | | 25 d | — | 3 hr |
| 5RP8/6 | | 72 hr | 22 hr | 1 hr |
| 5RP9/2 | 336 hr | 22 hr | 1 hr | 30 min |

Figure 2:
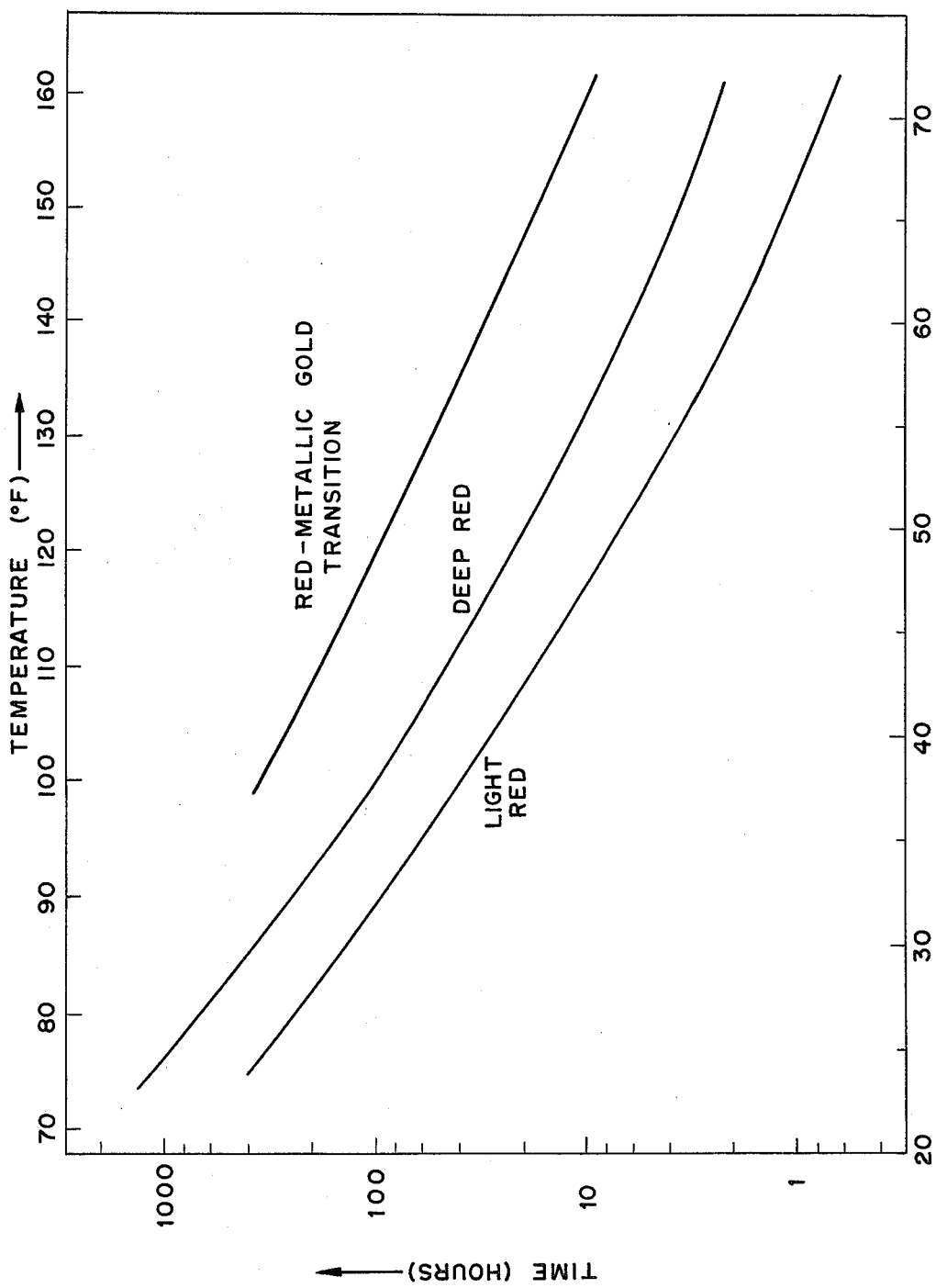
FIG. 2 is a plot, on coordinates of time in hrs and temperature in ° C and ° F, depicting isochromatic responses of a time-temperature history indicator (comprising 2,4-hexadiyne-1,6diol-bis-p-toluene sulfonate deposited on filter paper by evaporation of the solvent, ethyl acetate, from an absorbed solution) exposed to various time-temperature combinations.

These color changes are graphically depicted in FIG. 2, which is a plot depicting isochromatic responses as a function of time and temperature.

EXAMPLE 3

Polymers of the type

[-C ≡ C-$(CH_2)_m$OCONH$(CH_2)_6$N-HOCOCH$_2$$(CH_2)_m$-C ≡ C-]$_n$, where m is 2, 3 or 4 and n is large, corresponding to a high polymer, were formed by addition reactions between hexamethylene diisocyanate and the respective diol.

These polymers strongly adhered to glass and to metal surfaces after solvent or melt deposition on these surfaces. For m = 2, the initial color was a light pink. For m = 3 or 4, the initial color was a light blue. The polymers were exposed to 135° C in the dark and rapidly cooled to room temperature for examination. For m = 2, the color turned red-purple after 2 hr. For m = 3, the color turned blue-purple after 2 hr. For m = 4, the color turned light brown after 2 hr.

Green colored filter paper was also employed, with similar results obtained, except that the initial color was green. Green colored filter paper is useful because of the conventional association of green and red with "proceed" and "stop," respectively. With respect to perishables, such colors might be chosen to indicate whether to proceed with usage or to stop usage because of degradation.

EXAMPLE 5

Employing a Cadiot-Chodkiewicz-type reaction, 3-bromopropyne-1-ol was reacted with 1,5-hexadiyne to give two products, 2,4,8-nonatriyne-1-ol (I) and 2,4,8,10-dodecatetrayne-1,12-diol (II), which were separated by use of appropriate solvents. Oxidative coupling of (I) gave 2,4,8,10,14,16-octadecahexayne-1,18-diol (III).

Urethanes (—NHOCO—) of (I), (II) and (III) were obtained by addition-type reactions with the appropriate isocyanates. Benzoates ($C_6H_5$OCO—) and p-toluene sulfonates (p-$CH_3$-$C_6H_4SO_3$—) were formed by employing a Schotten-Bauman-type reaction; the former reaction used pyridine and the latter, potassium hydroxide.

The following materials in powder form were tested at the times and temperatures indicated with the results listed in Table II below:

TABLE II

| Composition, Color as Formed and Crystallization Solvent | Color change after: | |
|---|---|---|
| | 16 hr at 25° C in day light | indicated time periods at 5° C in the dark |
| $CH_3NHOCOCH_2-C{\equiv}C-C{\equiv}C-(CH_2)_2-C{\equiv}CH$ (white) ($CH_3OH/H_2O$) | none; pink (4 mo) | little change (1 mo); light pink (4 mo) |
| $C_2H_5NHOCOCH_2-C{\equiv}C-C{\equiv}C-(CH_2)_2-C{\equiv}CH$ (white) ($CH_3OH/H_2O$) | none; light pink (4 mo) | little change (1 mo) very light pink (4 mo) |
| $C_6H_5OCOCH_2-C{\equiv}C-C{\equiv}C-(CH_2)_2-C{\equiv}CH$ (white) ($CH_3OH$) | none | none (1 mo) |
| $C_6H_5OCOCH_2-C{\equiv}C-C{\equiv}C-(CH_2)_2-C{\equiv}CH$ (white) (pet. ether, 60°–110° C) | " | little change (1 mo.) |

TABLE II-continued

| Composition, Color as Formed and Crystallization Solvent | Color change after: 16 hr at 25° C in day light | indicated time periods at 5° C in the dark |
|---|---|---|
| p-CH$_3$—C$_6$H$_4$SO$_3$CH$_2$—C≡C—C≡C—(CH$_2$)$_2$—C≡CH (white) (CH$_3$OH) | " | " |
| (1) [CH$_3$NHOCOCH$_2$—C≡C—C≡C—CH$_2$—]$_2$ (red) (acetone/pet. ether, 60°–110° C) | red-purple | red-purple (16 hr) |
| [C$_2$H$_5$NHOCOCH$_2$—C≡C—C≡C—CH$_2$—]$_2$ (white) (acetone/pet. ether, 60°–110° C) | none; light red (4 mo) | none (2 wk); very light pink (4 mo) |
| [C$_6$H$_5$NHOCOCH$_2$—C≡C—C≡C—CH$_2$—]$_2$ (light pink) (acetone/CH$_3$OH) | red-purple | light pink (2 wk) |
| [C$_6$H$_5$OCOCH$_2$—C≡C—C≡C—CH$_2$—]$_2$ (white) (acetone/CH$_3$OH) | none | none (2 wk) |
| [p-CH$_3$—C$_6$H$_4$SO$_3$CH$_2$—C≡C—C≡C—CH$_2$—]$_2$ (light tan) (ethyl acetate/CH$_3$OH) | none | none (2 wk) |
| (2) [CH$_3$NHOCOCH$_2$—C≡C—C≡C—(CH$_2$)$_2$—C≡C—]$_2$ (red) (acetone/pet. ether, 60°–110° C) | blue-red | blue-red (16 hr) |
| [C$_2$H$_5$NHOCOCH$_2$—C≡C—C≡C—(CH$_2$)$_2$—C≡C—]$_2$ (white) (acetone/pet. ether, 60°–110° C) | medium pink | light pink (2 wk) |
| [C$_6$H$_5$NHOCOCH$_2$—C≡C—C≡C—(CH$_2$)$_2$—C≡C—]$_2$ (white) (acetone) | light pink | rose-red (2 wk) |
| [C$_6$H$_5$OCOCH$_2$—C≡C—C≡C—(CH$_2$)$_2$—C≡C—]$_2$ (white) (acetone/CH$_3$OH) | none | none (2 wk) |
| [p-CH$_3$—C$_6$H$_4$SO$_3$CH$_2$C≡C—C≡C—(CH$_2$)$_2$—C≡C—]$_2$ (tan) (ethylacetate/pet. ether, 60°–110° C) | red | red (16 hr) |

(1) turns very light red at 100° C after 10 min turns light red at 115° C after 10 min turns red-purple at 125° C after 15 min
(2) turns light purple at 100° C after 10 min turns medium purple at 115° C after 10 min turns dark purple at 125° C after 10 min

EXAMPLE 6

Diacetylenes of the form [R-C≡C-]$_2$ were prepared by a conventional reaction of the corresponding diol and isocyanate. Solutions of the various diacetylenes were prepared in a variety of solvents and deposited as in Example 1 on white filter paper. Following drying, the color at various times $t$ and temperatures T was noted. Those results are tabulated below in Table III. The as-formed compositions, before thermal history development, were colorless.

TABLE III

| R | Solvent | Concentration | T, ° C | t, hr | Color |
|---|---|---|---|---|---|
| C$_2$H$_5$NHOCOCH$_2$— | methanol | 20% | 25 | 960 | light pink |
| | | | 40 | 960 | pink |
| | | | 50 | 960 | metallic copper |
| | | | 60 | 288 | " |
| | | | 70 | 75 | " |
| | carbon tetrachloride | 20% | 25 | 16 | colorless |
| | | | 70 | 16 | light blue-pink |
| | bromoform | 20% | 25 | 16 | colorless |
| | | | 70 | 16 | light blue-pink |
| | dichloromethane | 20% | 25 | 16 | colorless |
| | | | 70 | 16 | light blue-pink |
| n-C$_4$H$_9$NHOCOCH$_2$— | bromoform | 20% | 25 | 16 | light blue |
| | | | 70 | 16 | red |
| | carbon tetrachloride | 20% | 25 | 16 | light blue |
| | | | 70 | 16 | red |
| | isopropyl ether | 20% | 25 | 16 | light blue |
| | | | 70 | 16 | red |
| | dichloromethane | 20% | 25 | 16 | light blue |
| | | | 70 | 16 | red |
| C$_6$H$_5$NHOCOCH$_2$— | p-dioxane | 20% | 25 | 115 | blue |
| | | | 40 | 67 | red |
| | | | 50 | 22 | " |
| | | | 60 | 8 | " |
| | bromoform | 20% | 25 | 16 | colorless |
| | | | 70 | 16 | very light pink |
| p-CH$_3$—C$_6$H$_4$SO$_3$CH$_2$— | acetone | 0.5% | 40 | 68 | light red |
| | | | 50 | 68 | dark red |
| | | | 60 | 68 | metallic gold |
| | | | 70 | 68 | " |
| | ethylacetate | 20% | 23 | 960 | red |
| | | | 40 | 250 | metallic gold |
| | | | 50 | 85 | " |
| | | | 60 | 32 | " |
| | | | 70 | 11 | " |
| | chloroform | 10% | 70 | 3 | pink |
| | | | 70 | 16 | red |
| | bromoform | 10% | 70 | 3 | pink |
| | | | 70 | 16 | gold |
| | acetone | 5% | 70 | 3 | pink |
| | | | 70 | 16 | gold |
| | carbon tetrachloride | 5% | 70 | 3 | pink |
| | | | 70 | 16 | gold |
| | dimethyl | 5% | 70 | 3 | colorless |

TABLE III-continued

| R | Solvent | Concentration | T, °C | t, hr | Color |
|---|---|---|---|---|---|
| | formamide | | 70 | 16 | colorless |
| $C_2H_5NHOCO(CH_2)_2-$ | acetone | 5% | 70 | 16 | very light pink |
| | | 2% | 120 | 0.2 | light red |
| | ethylacetate | 2% | 120 | 0.2 | light red |
| | p-dioxane | 2% | 120 | 0.2 | light red |
| | tetrahydro-furan | 2% | 120 | 0.2 | light red |
| | acetone/ ethylacetate | 2% | 120 | 0.2 | light red |
| | dichloromethane | 20% | 25 | 16 | colorless |
| | | | 70 | 16 | very light pink |
| | bromoform | 20% | 25 | 16 | colorless |
| | | | 70 | 16 | very light pink |
| $CH_3NHOCO(CH_2)_4-$ | tetrahydro-furane | 2% | 120 | 0.5 | violet |
| | p-dioxane | 2% | 120 | 0.5 | violet |
| | glyme | 2% | 120 | 0.2 | violet |

EXAMPLE 7

Sodium amide at low temperature in an ammonia media was reacted with 1,4-dichlorobutyne, then with p-formaldehyde. Extraction with diethyl ether gave 2,4-pentadiyne-1-ol.

Oxidative coupling gave 2,4,6,8-decatetrazne-1,10-diol. After recrystallization from chloroform, this compound was reacted with ethyl isocyanate to give the desired urethane, $[C_2H_5NHOCOCH_2C \equiv C-C \equiv C-]_2$.

One inch squares of Whitman No. 42 filter paper were soaked in a 1% solution of the urethane in acetone and dried in the dark. The indicator sheets were then annealed in the dark at temperatures of −26°, −8°, 24° and 50° C. Color development was determined periodically by matching the indicator color to a Munsell Photometer Chart, with results as listed in Table IV below:

TABLE IV

| Munsell Color Code | Temperature, °C | | | |
|---|---|---|---|---|
| | −26° | −8° | 24° | 50° |
| 5Y4/4 | | | 28 d | 72 hr |
| N2/ | — | | | 2.5 hr |
| 5B3/4 | | 84 d | 72 hr | 2 hr |
| 5PB3/8 | | — | 21 hr | 50 min |
| 5PB4/10 | | — | 5 hr | 40 min |
| 5B4/6 | | 49 d | 4 hr | 30 min |
| 5B5/6 | | 28 d | 3 hr | 20 min |
| 5B6/6 | | — | 2 hr | 10 min |
| 5B7/6 | 104 d | — | 1.5 hr | — |
| 5B8/4 | 60 d | 72 hr | 20 min | — |
| 5B9/2 | 40 d | 24 hr | — | — |

EXAMPLE 8

The following experiments were performed to demonstrate that the thermal reactivity of certain acetylenic compounds can be dramatically increased by low temperature γ-ray irradiation. The initially colorless compounds were sealed in vacuum and irradiated at liquid nitrogen temperature with 50 Mrad of $Co^{60}$ γ-rays at 1 Mrad/hr. After irradiation, the color of the samples was noted before and 5 to 10 min after the samples were removed from the liquid nitrogen.

The compound $[C_6H_5NHOCO(CH_2)_4-C \equiv C-]_2$, which was crystallized by cooling a saturated ethyl acetate solution, was tan colored immediately after irradiation, but turned reddish bronze within 5 to 10 min after removal from the liquid nitrogen.

The compound $C_6H_5(CH_2)_2C \equiv C-C \equiv C-CH_2OCONHC_2H_5$, which was crystallized by cooling a saturated petroleum ether (60°–110° C fraction) solution, was light tan immediately after irradiation, but turned metallic gold within 5 to 10 min after removal from the liquid nitrogen. In both cases, the observed color change was irreversible.

What is claimed is:
1. A process which comprises applying to a perishable product an integral time-temperature history indicator comprising at least one acetylenic compound having at least two conjugated acetylene groups per molecule.
2. The process of claim 1 in which the acetylenic compound is deposited on a substrate affixed to the product.
3. The process of claim 1 in which the acetylenic compound is deposited on the product.
4. The process of claim 1 in which the acetylenic compound is applied from a solution of the acetylenic compound in a solvent and the solvent is evaporated from the solution.
5. The process of claim 1 in which the thermal reactivity of the acetylenic compound is increased by low temperature exposure to actinic radiation.
6. The process of claim 1 in which the acetylenic compound is selected from the group consisting of diynes, triynes, tetraynes and hexaynes.
7. The process of claim 1 in which the acetylenic compound contains at least one substituent selected from the group consisting of alkyl, aryl, sulfonate, urethane, acid and alcohol derivatives.
8. The process of claim 1 in which a UV filter is incorporated in the indicator.
9. The process of claim 1 which further comprises deactivating an integral time-temperature thermal history indicator comprising at least one acetylenic compound having at least two conjugated acetylene groups per molecule.
10. The process of claim 9 which comprises inducing a phase change from an active phase to a substantially inactive phase.
11. The process of claim 10 in which the phase change is induced by applying a mechanical stress.
12. The process of claim 10 in which the acetylenic compound is rapidly heated to a temperature above its melting point.
13. The process of claim 9 in which unreacted acetylenic compound is extracted by a solvent.
14. The process of claim 9 in which unreacted acetylenic compound is removed by sublimation.

15. The process of claim 9 in which unreacted acetylenic compound is deactivated by donor-acceptor complex formation.

16. The process of claim 9 in which unreacted acetylenic compound is deactivated by a chemical reaction which eliminates the conjugated acetylene groups.

17. A perishable product having applied thereto an integral time-temperature history indicator comprising at least one acetylenic compound having at least two conjugated acetylene groups per molecule.

18. The product of claim 17 in which the acetylenic compound is selected from the group consisting of diynes, triynes, tetraynes and hexaynes.

19. The product of claim 17 in which the acetylenic compound contains at least one substituent selected from the group consisting of alkyl, aryl, sulfonate, urethane, acid and alcohol derivatives.

* * * * *